(12) United States Patent
Shapiro et al.

(10) Patent No.: US 9,044,598 B2
(45) Date of Patent: Jun. 2, 2015

(54) SMART LASER BIO-SENSOR AND BIO-THERAPEUTIC DEVICE SYSTEM AND METHODS

(76) Inventors: Ronald S. Shapiro, Toledo, OH (US); David B. Sutton, Monroe, MI (US)

(*) Notice: Subject to any disclaimer, the term of this patent is extended or adjusted under 35 U.S.C. 154(b) by 0 days.

(21) Appl. No.: 13/462,528

(22) Filed: May 2, 2012

(65) Prior Publication Data

US 2012/0283603 A1 Nov. 8, 2012

Related U.S. Application Data

(60) Provisional application No. 61/481,507, filed on May 2, 2011.

(51) Int. Cl.
| | |
|---|---|
| *A61H 1/00* | (2006.01) |
| *A61N 5/06* | (2006.01) |
| *A61N 7/00* | (2006.01) |
| *A61F 7/00* | (2006.01) |
| *A61B 18/00* | (2006.01) |

(52) U.S. Cl.
CPC ............. *A61N 5/0625* (2013.01); *A61N 7/00* (2013.01); *A61F 7/007* (2013.01); *A61B 2018/00642* (2013.01); *A61F 2007/0071* (2013.01); *A61F 2007/0093* (2013.01); *A61F 2007/0096* (2013.01); *A61N 2007/0026* (2013.01); *A61N 2005/0642* (2013.01)

(58) Field of Classification Search
CPC ............................. A61N 7/00; A61H 23/0245
USPC ............................................................ 601/2
See application file for complete search history.

(56) References Cited

U.S. PATENT DOCUMENTS

| | | | | |
|---|---|---|---|---|
| 4,528,979 A | * | 7/1985 | Marchenko et al. | 606/21 |
| 7,503,927 B1 | * | 3/2009 | Vetanze | 607/91 |
| 2008/0108982 A1 | * | 5/2008 | Barolet et al. | 606/9 |
| 2011/0144727 A1 | * | 6/2011 | Benedict | 607/91 |
| 2012/0191005 A1 | * | 7/2012 | Sobol et al. | 600/562 |

* cited by examiner

*Primary Examiner* — Tse Chen
*Assistant Examiner* — Hien Nguyen
(74) *Attorney, Agent, or Firm* — Ballard Spahr LLP (57) ABSTRACT

An apparatus includes a housing having a treatment surface, a light source disposed adjacent the treatment surface and configured to emit dynamic photonic energy, a thermal element disposed adjacent the treatment surface and configured to emit dynamic thermal kinetic energy, and a controller disposed in the housing, the controller in communication with the light source and the thermal element to vary a plurality of parameters of the light source and the thermal element to control the characteristics of the dynamic photonic energy and the dynamic thermal kinetic energy emitted thereby. The treatment surface can also house a variety of sensors that can capture a variety of physical and chemical data, which is integrated with a malleable energy composition and delivery system that co-ordinates with the treatment progress.

13 Claims, 9 Drawing Sheets

SMART LASER BIO-SENSOR AND BIO-THERAPEUTIC DEVICE SYSTEM AND METHODS

CROSS REFERENCE TO RELATED PATENT APPLICATION

This application claims priority to U.S. Provisional Application No. 61/481,507 filed May 2, 2011, herein incorporated by reference in its entirety.

FIELD OF INVENTION

The present disclosure relates generally to an apparatus, a system, and a method for therapy or treatment of a body of a user. In particular, the disclosure can be directed to a therapeutic device for emitting dynamic photonic energy and thermal kinetic energy to a treatment area of the body of the user.

BACKGROUND

Fragile joints are natural "shock absorbers" and take considerable abuse. Over 60 million persons in the United States between the ages of 20-60 have joint pain that limits performance and quality of life. Examples of common sources of knee pain are: i) Osteoarthritis, ii) obesity, iii) Patello-Femoral Syndrome, iv) Osgood-Schlatter disorder, v) Ligament strains and sprains, vi) Overuse syndromes, and vii) Plica Syndrome. In youth, joint wear and injury trigger toxicity we know as inflammation. This activates the immune system to help repair and promote healing. With age, and increased damage, this repair process slows and toxicity often accumulates damaging cartilage and soft tissue. This is known as Toxic Joint Syndrome. Toxic Joint Syndrome refers to unhealthy joints resulting from disease or injury. The degree of debility may vary; however, most individuals notice undesirable effects regarding their performance, functional abilities, and quality of life. Often, persons suffering from joint pain must tolerate pain and restricted performance while engaging in work and leisure activities. Moreover, sales of pain medications have exploded, though they are known to be potentially dangerous, ineffective, and potentially lethal. To add to the problem, analgesics and non-steroidal anti-inflammatory medications simply mask the pain and can produce long term multiple organ damage without enhancing healing or rehabilitation. It is also well known that a growing population of consumers are building a reliance on pain medication for a variety of pain and joint related problems that can be habit forming and even lethal.

A number of devices on the market use various light technologies and offer minimal to moderate therapeutic benefit. The light emitted by such devices is static, non-dynamic light. This in itself is a significant impediment to short and long term therapeutic benefit. Not only may the therapeutic spectrum be limited, but use of these technologies with time fails to overcome the natural adaptive mechanisms of the human nervous system. This physiologic phenomenon known as tachypylasis reduces the effect of stimuli to the body, making many medications and therapies less effective over time. Not infrequently, this can result in incidences of over medication.

It would be desirable to have an apparatus, system, and method for treatment of a body of a user, wherein the treatment includes the application of at least a dynamic photonic energy and a thermal kinetic energy to the body of the user.

SUMMARY OF THE INVENTION

Concordant and consistent with the present invention, an apparatus, system, and method for treatment of a body of a user, wherein the treatment includes the application of at least a dynamic photonic energy and a thermal kinetic energy to the body of the user, has surprisingly been discovered.

The apparatus, systems and methods of the present disclosure can use dynamic energies to recuperative systems a gentle boost simulating youth. When applied to the surface area the treatment or therapy apparatus can collect data from the injured joint and can calculate a digital prescription especially formulated for the user's condition that is delivered through the soft tissue often avoiding the potential harmful effects of pain medication.

In an aspect, an apparatus can comprise: a substantially rigid housing with a lower portion and an upper portion, the lower portion of the housing having a substantially curvilinear shape; a flexible circuit board disposed in a cavity formed in the lower portion of the housing; a light source in electrical communication with the circuit board and configured to emit dynamic photonic energy; a thermal element in electrical communication with and configured to emit dynamic thermal kinetic energy; a sonic element in electrical communication with and configured to emit dynamic subliminal ultrasonic energy; a controller disposed in the housing, the controller in communication with the light source, the thermal element, and the sonic element to vary one or more parameters of the light source, the thermal element, and the sonic element to control the characteristics of one or more of the dynamic photonic energy, the dynamic thermal kinetic energy, and the dynamic subliminal ultrasonic energy emitted respectively thereby; and a sensor in electrical communication with the circuit board and the controller to form a feedback loop, wherein the controller provides electrical energy to one or more of the light source, the heating element, and the sonic element in response to a signal received from the sensor.

In an aspect, an apparatus can comprises: a housing having a treatment surface; a light source disposed adjacent the treatment surface and configured to emit dynamic photonic energy; a thermal element disposed adjacent the treatment surface and configured to emit dynamic thermal energy; and a controller disposed in the housing, the controller in communication with the light source and the thermal element to automatically vary a plurality of parameters of the light source and the thermal element to control the characteristics of the dynamic photonic energy and the dynamic thermal energy emitted thereby.

In an aspect, a system can comprise: a therapy device including a housing having a treatment surface, a light source disposed adjacent the treatment surface and configured to emit dynamic photonic energy, a thermal element disposed adjacent the treatment surface and configured to emit dynamic thermal kinetic energy, and a controller disposed in the housing, the controller in communication with the light source and the thermal element to vary a plurality of parameters of the light source and the thermal element to control the characteristics of the dynamic photonic energy and the dynamic thermal kinetic energy emitted thereby; and a base station including an electrical circuit configured to provide electrical energy to the therapy device when the therapy device is in electrical communication therewith Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems. The above, as well as other advantages of the present invention, will become readily apparent to those skilled in the art from the following detailed description of the preferred embodiment when considered in the light of the accompanying drawings in which.

DETAILED DESCRIPTION OF EXEMPLARY EMBODIMENTS OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

In an aspect, photonic energy can refer to particles of light (photons) that are employed using a variety of multiple wavelengths. As an example, photonic energy can comprise transmission of particles in one or more of the visible and invisible spectrum. As a further example, particles can be employed using a plurality of parameters, including, but not limited to: magnitude (joules), patterns, sweeps, cascades, duty cycles, frequencies, alternations, and time. In an aspect, the parameters of the photonic energy transmission can change thousands of times per second.

In an aspect photon packets are employed using a variety of wave lengths (550→1000 nanometers). These multi-spectrum packets of electromagnetic (or light) energy are deployed using a variety of parameters (i.e. duty cycle, patterns, sweeps, sweep frequency, intensity, variable coherence, angle, integration with thermal components, timing, etc.) These parameters change thousands of times per second.

In an aspect, an operating system can incorporate feedback information from sensors (thermistors, EMG, infrared and, moisture) located in/on a treatment module. As an example, the operating system can utilize an "electronic energy prescription" (Veriscription™) to deploy the energy package which includes one or more of photonic energy, thermal kinetic energy, and dynamic subliminal ultrasonic energy to the body surface. Algorithms can govern the Veriscription and can automatically and continuously adjust the treatment for a specified treatment area and condition (e.g., mode selection).

In an aspect, thermal kinetic energy can be generated from duel sources: ambient photo and resistance. Other source(s) can be used. As an example, thermal properties can be manipulated through multiple cycles; deployed in changing joule packets; and/or delivered in concert with the Photonic components. Thermal kinetic energy is dynamic, in contrast to static heat.

In an aspect, joules of heat are generated from multiple sources: Resistance Heat: produced by Resistors, Ambient Heat: produced by LEDS, and/or Thermal Mass Heat: produced by Enclosure (heat contained in vessels).

In an aspect, dynamic subliminal ultrasonic energy can be a dynamic form of sound waves not audible to the human ear. As an example, ultrasonic waves can be employed in a way that they are neither heard nor felt. As a further example, subliminal ultrasonic energy can be delivered using multiple and varying parameters. In an aspect, sound waves can be used utilized and manipulated in such a fashion as to not damage tissue (e.g., cavitation). In an aspect, dynamic subliminal ultrasonic energy can comprise variable parameters including: Frequency (e.g., 0.8 MHZ to 4 MHZ); Timing (e.g., 1-10 millisecond bursts—variable off and on through treatment cycle); Intensity (e.g., continuous or from 10% to 100% ultrasound delivery); and Focus (narrow to broad beam).

In an aspect, sonic parameters can be automatically and constantly changed which provides dynamic properties. The dynamic subliminal ultrasonic energy is integrated in concert with the other energies (photonic and thermal kinetic described above) to produce additional and enhanced therapeutic effects.

In an aspect, biosensory feedback looping can be used. As an example, multiple bio-sensors (e.g., thermistor, electrode, infrared mapping device, etc) are positioned in a treatment surface of device. Additional sensory technology can include measurements of blood flow, thermal mapping, chemical substance levels (e.g. nitric oxide, pH, lactic acid, etc.), fluid volume, fluid density, and particulate matter. This can provide measurable data before and after treatment that will provide guidance on the improvement of the user's condition.

An operating system, processor, computing device, and/or software can compute information relating to one or more of an area of treatment, treatment mode selected, energy levels, biosensory data, etc. As an example, customized treatment can be delivered at the skin surface to the selected area. As a further example, as a result of this highly developed computerized system, the phenomenon of tachyphylaxis (adaptation by the body to repeated stimuli/treatment) is overcome. Accordingly, treatment time can be unlimited and/or treatment frequency can be unlimited. Favorable results have been achieved, whereby pain is minimized, circulation is maximized, mobility is improved, and performance is enhanced.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

FIGS. 1-7 illustrate a therapy system 10 according to an embodiment of the present disclosure. As shown, the therapy system 10 includes a therapy device 12 or apparatus and a base station 14, wherein the therapy device 12 can be releaseably and selectively coupled to the base station 14 for storage and/or charging. It is understood that the therapy system 10 can include additional components and treatment components such as a treatment gel, for example.

As more clearly shown in FIGS. 8-14, the therapy device 12 can have a substantially rigid housing 16 with a lower portion 18 and an upper portion 20. In the embodiment shown, the lower portion 18 of the housing 16 has a substantially curvilinear shape defining a treatment surface 22. In certain embodiments, the lower portion 18 of the housing 16 has a pre-determined substantially semi-circular shape having a radial center-point CP. However, it is understood that the lower portion 18 of the housing 16 can have any size and shape.

In certain embodiments, an outer wall 24 of the lower portion 18 of the housing 16 can include a mechanism 26 for securing the therapy device 12 to a patient during use. As a non-limiting example, the securing mechanism 26 includes a pair of generally circular discs 28, each of the discs 28 coupled to an elongate tab 30 or protrusion extending from the outer wall 24 of the lower portion 18 of the housing 16. Typically, the discs 28 have a larger radius than a radius or width of the associated tab 30. Accordingly, a strap (not shown) can be positioned around a portion of a circumference of each of the tabs 30 and secured in position by the disc 28 coupled thereto, as appreciated by one skilled in the art. The strap can then be positioned around a portion of a body of the user to secure the therapy device 12 in a generally static position relative to the body of the user. It is understood that the securing mechanism 26 can have any shape and size. It is further understood that other means of securing the therapy device 12 to the user can be used.

In certain embodiments, a cavity 32 can be formed in the treatment surface 22 of the lower portion 18 of the housing 16. As a non-limiting example, a circuit board 34 is disposed adjacent/in the cavity 32. As a further non-limiting example, the circuit board 34 is a flexible circuit board. An example of a suitable circuit board is manufactured by Century Circuits. The circuit board 34 is typically in electrical communication with a source of electrical energy 36 in a manner that is well known in the art. As a non-limiting example, the source of electrical energy 36 is a removable and rechargeable battery pack (e.g. accessible via a battery plate 37 removably coupled to the housing 16). The circuit board 34 is configured so that various electrical components can be connected to the circuit board 34 whereby electrical energy can be supplied to the various components in a manner to activate and control the electrical components.

A plurality of light emitting diodes (LEDs) 38 can be operatively connected to the circuit board 34 to selectively energize the LEDs 38. As a non-limiting example, the LEDs 38 are positioned in the cavity 32 and configured to emit photonic energy outwardly from the cavity 32. In certain embodiments, the LEDs 38 are mounted on the circuit board 34. It is understood that the LEDs 38 can be positioned in any configuration to allow a photonic energy to be emitted therefrom and directed toward the user. As a further non-limiting example, photonic energy is defined as a dynamic form of electromagnetic radiation, wherein particles of light (photons) are emitted having a variety of wave lengths (both in the visible and invisible spectra). Specifically, each of the LEDs 38 can be controlled to change the parameters of photons emitted therefrom thousands of times per second. In certain embodiments, a plurality of photons is emitted as a photon packet, wherein each photon of the photon packet has similar parameters and photonic characteristics. As a non-limiting example, each of the photons or photo packets is emitted having a variable wavelength ranging from 550-1000 nanometers. As a further non-limiting example, each of the photons or photon packets is deployed having a variety of controlled parameters (i.e. duty cycle, patterns, sweeps, sweep frequency, intensity, variable coherence, angle, integration with thermal components, timing, etc.). It is understood that the parameters of each photon or photon packet can be varied. It is further understood that the parameters of each photon or photon packet are automatically varied multiple times per second (e.g. from one hundred to over one thousand times per second).

A plurality of thermal elements 40 can be operatively connected to the circuit board 34 and positioned adjacent the LEDs 38. As a non-limiting example, the thermal elements 40 are resistive heating elements such as resistors manufactured by the Vishay/Dale. As a further non-limiting example, the thermal elements 40 are configured to extend from the cavity 32 in a similar manner as the LEDs 38. Accordingly, the thermal elements 40 are disposed adjacent a surface of the user that is to be treated during a treatment process. In certain embodiments, the thermal elements 40 are mounted on the circuit board 34. The thermal elements 40 can be selectively and dynamically activated by the circuit board 34 to impart a thermal kinetic energy to the surface that is being treated. As a non-limiting example, thermal kinetic energy is defined as a dynamic form of heat. In the embodiment shown, the thermal kinetic energy is generated from at least three sources, namely, a direct energy from the thermal elements 40, an ambient energy from the other elements (e.g. LEDs 38) of the therapy device 12, and a thermal mass heat produced by enclosure (heat contained in vessels). The overall thermal kinetic energy is controlled by varying the thermal characteristics of at least one of the sources of thermal kinetic energy. As a non-limiting example, the thermal elements 40 can be controlled through multiple cycles of dynamic joule packets, wherein each "joule packet" represents a discrete amount of calculated heat delivered in concert with the ambient heat of the LEDs 38. It is understood that each joule packet can be automatically varied multiple times per second to provide a dynamic treatment.

In certain embodiments, the therapy device 12 can include a plurality of sonic elements 42 operatively connected to the circuit board 34 and positioned adjacent at least one of the LEDs 38 and the thermal elements 40. The sonic elements 42 are configured to emit a dynamic subliminal ultrasonic energy. As a non-limiting example, the dynamic subliminal ultrasonic energy is defined as a dynamic form of sound waves not audible to the human ear. As a further non-limiting example, the dynamic subliminal ultrasonic energy is embodied by a plurality of ultrasonic waves emitted in a manner that is neither heard nor "felt" by the user. The dynamic subliminal ultrasonic energy is typically delivered using multiple and varying parameters. As a non-limiting example, variable parameters of the sonic elements 42 include: frequency (0.8 MHZ to 4 MHZ); timing (1-10 millisecond bursts—variable off and on through treatment cycle); intensity (continuous or from 10% to 100% ultrasound delivery); and focus (narrow to broad beam). In certain embodiments, the parameters of the sonic elements 42 are automatically and constantly changed to provide dynamic properties in concert with the photonic and thermal kinetic energies.

In certain embodiments, a plurality of thermistors 44 can be operatively connected to the circuit board 34 and are positioned to be adjacent the LEDs 38. The thermistors 44 are designed to measure the temperature on the surface that is being treated by the therapy device 12. In certain embodiments, the thermistors 44 are mounted on the circuit board 34 in a manner that allows the thermistors 44 to effectively monitor the temperature on the entire surface that is being treated by the therapy device 12. The thermistors 44 can measure temperature of a surface segmentally or averaged for the entire surface that is being treated. In certain embodiments, the circuit board 34 provides a feedback loop that reacts to the temperature readings, and multiple or individual readings obtained in regard to a variety of physical and chemical elements. The technology "learns" from the sensory information collected and adjusts the energy supplied to the LEDs 38 and thermal elements 40 to maintain the desired therapeutic energy delivery on the surface being treated. Moreover as the operating system incorporates the discovered sensory information, it can continuously adjusts the therapeutic energy formula. In other words, the device can "learn" the continuously changing status of the individual being treated, and it continuously changes and adapts the therapeutic multiple energy formula in concert with the learned information and the changing conditions. In addition, the some or all of the sensory discovered parameters may be displayed on the LCD screen, stored in memory, or uploaded wirelessly or wired, to another computer or the internet.

In certain embodiments, a plurality of electrodes 46 can be operatively connected to the circuit board 34 in the same manner as the LEDs 38 and thermal elements 40 previously described. Electrodes made by the Vishay/Dale Company can be used with the therapy device 12. The electrodes 46 are utilized to detect the electrical currents that are generated in an active muscle that is receiving treatment from the therapy device 12. It is understood that other sensors and feedback devices can be included such as: infrared heat sensors with pre- and post-Rx for thermal mapping; sound sensors with pre- and post-Rx for sonic mapping of pre- and post-origination of measurements including the radiant pattern of the pain and post treatment measurement; Electroencephalography (EEG) sensors to measure pre- and post-Tx muscle tension and activity; and a camera to measure distance of flexion excursion (could use radar like technology and digital and graphic display reporting and mapping).

As a non-limiting example, a cover 48 or encapsulant can be positioned over the LEDs 38, the thermal elements 40, the sonic elements 42, the thermistors 44 and the electrodes 46 to separate these elements from the environment in which the therapy device 12 is used. An example of the cover 48 is an infra-red transparent material. A non-limiting example is D9930 doming material produced by Epic. The cover 48 is also impervious to bacteria, viruses, and debris and provides a flexible barrier and protects the electronic components from environmental contaminants when the therapy device 12 is utilized to provide dynamic photonic and kinetic thermal stimulation. The cover 48 can also have a traction surface for providing a friction or adhesion between the treatment surface 22 and the body of the user. In certain embodiments, a soft, disposable strip of rubber or foam material is positioned on the housing 16 to provide comfort from the pressure from the housing 16 of the firmly attached therapy device 12.

The upper portion 20 of the housing 16 can include a user interface 50 in electrical communication with a controller 52. As shown, the user interface 50 includes a display 54, a plurality of user-engageable buttons 56, and an interface data port 58. It is understood that the user interface 50 can include other interface elements such as, lights, audio elements and user-controlled elements.

The display 54 can be any means for providing a visual feedback to the user. As a non-limiting example, the display 54 is a liquid crystal display (LCD) to present information to the user such as currently used parameters, bio-sensor feedback, a graphical display of the pattern and sequencing of the LEDs 38 (or other components), and other digital and graphical information. The display 54 is typically in data communication with the controller 52 to receive data signals therefrom to control the information being presented to the user.

The user-engageable buttons 56 provide a means for the user to control the components of the therapy device 12. Typically, the user-engageable buttons 56 are in communication with the controller 52 to allow the user to provide a control input to the controller 52, thereby affecting the operation of the therapy device 12. As a non-limiting example, a power button can be included, wherein the power button activates or deactivates the therapy device 12. As a further non-limiting example, a mode button is provided to select treatment settings, which define a pre-set range of parameters for the components of the therapy device 12.

The interface data port 58 can be any data interface (wired or wireless) for providing intercommunication between the therapy device 12 and a secondary device or system (not shown) such as a personal computer, the Internet, a remote server, a physician's office computer, and the like. It is understood that software can be provided to facilitate the secure transfer and/or analysis of the data received from the therapy device 12. It is further understood that data can be transferred to the therapy device 12 from a secondary source. It is further understood that the interface data port 58 can be integrated with the base station 14.

In certain embodiments, the controller 52 is enclosed within the upper portion 20 of the housing 16. However, it is understood that the controller 52 can be positioned within the lower portion 18 of the housing 16. The controller 52 is operatively connected to the circuit board 34 for controlling a supply of electrical energy to a variety of electrical components and in particular the LEDs 38, the thermal elements 40, and the sonic elements 42. The controller 52 is designed to provide a wide range of operational characteristics for the LEDs 38 including allowing the LEDs 38 to be sequenced in the activated mode to satisfy various operating parameters that will enhance the delivery of the photonic energy to the user of the therapy device 12. Further, the controller 52 is configured to receive feedback signals from the various sensors and measurement devices including the thermistors 44 and the electrodes 46.

As more clearly shown in FIGS. 15-21, the base station 14 can include a housing 60 with a lower surface 62 and an upper surface 64. In the embodiment shown, a plurality of feet 66 is coupled to (or formed on) the lower surface 62 to protect the lower surface 62 of the housing 60, while providing traction between the housing 60 and a secondary (e.g. substantially static) surface (e.g. a counter, a table, and the like).

In the embodiment shown, the base station 14 includes an electrical circuit 68 interposed between a secondary source of electrical energy 70 and a plurality of electrical terminals 72. As a non-limiting example, the source of electrical energy 36 can be electrically coupled to the electrical circuit 68 of the base station 14 for charging, independent of the therapy device 12.

In certain embodiments, the electrical terminals 72 are aligned with a plurality of charging terminals 74 formed in/on the housing 16 of the therapy device 12 to charge the therapy device 12 (i.e. the source of electrical energy 36), while the therapy device 12 is mechanically coupled to the base station or "docked". It is understood that other means of charging the source of electrical energy 36 can be used. It is further understood that the secondary source of electrical energy 70 can be remote from the base station 14 and in electrical communication with the electrical circuit 68 via an electrical conductor (e.g. a wire or converter).

In operation, the therapy device 12 is positioned on the surface that is to receive treatment. The controller 52 is operatively connected to the circuit board 34 for controlling the supply of electrical energy to a variety of electrical components including the LEDs 38, the thermal elements 40, and the sonic elements 42. It is understood that the source of electrical energy 36 can be a portable battery pack to allow the therapy device 12 to be used without cords.

As a non-limiting example, the controller 52 controls the LEDs 38 so that the LEDs 38 are activated in various geometrical patterns. The controller 52 can also be utilized to establish the rate that each of the LEDs 38 or a cluster of the LEDs 38 is electrically activated and deactivated. The pattern and rate at which the LEDs 38 are activated and then deactivated can be controlled by the controller 52 to produce the desired treatment results for the user of the therapy device 12. In particular, the controller 52 can provide a variable refresh rate for the therapy device 12 which cycles how often the pattern of the treatment modalities is repeated. Each of the LEDs 38 can be individually sequenced, and sequenced in various patterns, sequenced in multiple and variable sweep times, sequenced with accompanying variable thermal energy. Each of the LEDs 38 can be automatically varied to emit visible and invisible light.

The controller 52 can also be utilized to control the pattern and rate at which the thermal elements 40 are energized and deenergized by the circuit board 34. The pattern and rate at which the thermal elements 40 are energized and deenergized for the thermal elements 40 can established to be essentially the same as the pattern and rate for the LEDs 38 or the controller 52 can be utilized to operate the thermal elements 40 independently of the pattern and rate of the LEDs 38.

The controller 52 can also be utilized to control the pattern and rate at which the sonic elements 42 are energized and deenergized by the circuit board 34. The pattern and rate the sonic elements 42 are energized and deenergized can established to be essentially the same as the pattern and rate for the LEDs 38 or the controller 52 can be utilized to operate the sonic elements 42 independently of the pattern and rate of the LEDs 38.

The electrical currents that are detected by the electrodes 46 are sent to the controller 52 where an electromyographic instrument can be utilized to evaluate the electrical currents to determine the degree of muscle tension, contraction and relaxation in the muscles that are receiving treatment from the therapy device 12. The degree of muscle tension and contraction indicated by the electrodes 46 is used to establish treatment time or other treatment options. The degree of muscle tension and contraction provides measurable information on the status of the treatment that can be used to supplement the subjective reactions of the user to the treatment received by the therapy device 12.

The controller 52 (e.g. via an operating system or software) utilizes an "electronic energy prescription" (Veriscription™ electronic prescription) to deploy the treatment energy package which includes photonic energy, thermal kinetic energy, and dynamic subliminal ultrasonic energy to the body surface. As a non-limiting example, five proprietary algorithms govern the controller 52 to automatically and continuously adjust the treatment for the specified area and condition (i.e. Mode selection).

The controller 52 incorporates feedback information from sensors (e.g. temperature, electrical impulse, infrared, moisture, and the like) located in the therapy device 12. Customized treatment is delivered at the skin surface to the selected area. As a result of this highly developed computerized system: the phenomenon of tachyphylaxis (adaptation by the body to repeated stimuli/treatment) is overcome; treatment time is unlimited; and treatment frequency is unlimited.

The desired temperature for the surface that is being treated can be set with the controller 52 and the thermistors 44 measure the actual temperature of the surface and supply the temperature feedback information to the controller 52. The actual temperature can be compared to the desired temperature and the controller 52 can adjust the energy supplied to the thermal elements 40 to maintain the temperature on the surface that is being treated in the desired range. The thermal feedback provided by the thermistors 44 allows the heat energy provided by the surface that is being treated to be maintained at an effective and safe level. In addition, a biosensory feedback looping is provided to the controller from various biosensors positioned in the treatment surface 22 of the therapy device 12. It is also understood that adjustment of all the energy parameters can be governed by the learned information regarding a variety of physical and chemical readings discovered by the sensory elements in the treatment surface.

It is also realized that multiple areas of the human body have different and often unique anatomical composition, physiology, and form. Therefore, applications employing the present invention can vary between anatomical areas of the body and between species. Therefore, it should be understood that treatment energy ingredients, treatment parameters, composition, and delivery algorithms will be unique and proprietary to species, area, and condition such as: upper back—cervical/thoracic cast; low back—lumbosacral cast; a head (cranial) cast; smaller joint cast—wrist, ankle, hand and foot cast; Rx arthritis; plantar fasciitis; injury; hip cast; cranial cap; head pain; muscular pain; ligamentous pain; facial pain; neuritic pain i.e. occipital neuritis; facial/sinus cast; relieve sinus pain; facilitate sinus drainage; provide topical treatment to cutaneous structures; equine hock adaptor; and the like.

The mode selection enables the user to select the treatment that relates to the nature and location of their condition. For example, an injury or condition of a specific body area (i.e. the knee joint) of less than 30 hours duration requires a unique energy and sequencing pattern that integrates a specific heat range.

When the treatment surface is applied directly to the skin the energies imparted by the therapy device 12 propagate various chemical and physiological reactions which can also be utilized to help quantify the level of benefit the treatment is providing. For example, it is envisioned that software in the operating system of the controller 52 could be enhanced to include base line sensory and performance metrics measured and recorded before and after treatment. This information would demonstrate the benefit the user had received from the treatment therapy session, and can then be utilized to formulate and customize subsequent therapies. Furthermore, diagnostic results can be uploaded from the therapy system 12 to a remote location for detailed analysis. Additionally, programming updates can be downloaded to the controller 52.

In certain embodiments, a composition of a plurality pharmaceutically active agents is applied to a surface of the body of the user to penetrate the skin of the user in order to amplify the beneficial effects of the treatment of the therapy device 12. In particular, a treatment gel employs traditional components consisting of water, ethanol (ETOH) and glycerin to increase a skin moisture content. There are additional components in the gel which make the product unique and differentiate it from hand creams, lotions and balms that are currently on the market. These additional components and functional examples are provided below:

1) L arginine: loosens the bonds between cells of the stratum corneum (upper layer of skin) to facilitate the passage of photonic and thermal kinetic energy; and raises the potential for local generation of nitric oxide, which causes vasodilatation and attendant increased circulation.
2) Urea: thins and softens thick, damaged or devitalized skin to facilitate the passage of photonic and thermal kinetic energy; gently dissolves the intercellular matrix of skin to facilitate the passage of photonic and thermal kinetic energy; and provides a hyperosmolar environment to enhance intradermal moisture content to facilitate the passage of photonic and thermal kinetic energy.
3) Phosphatidyl Choline: augments the urea effect of thinning and softening of thick, damaged or devitalized skin to facilitate the passage of photonic and thermal kinetic energy; and augments the urea effect to promote dissolution of the intercellular matrix matrix of skin to facilitate the passage of photonic and thermal kinetic energy.

As a non-limiting example, the gel can include a transdermal "ketophrofen" (RS)2-(3-benzoylphenyl)-propionic acid (chemical formula C16H14O3) to deliver therapeutic anti-inflammatory and analgesic effects.

Favorable results have been achieved with embodiments of the gel having a variable pH from 5-8 and including a carbopol including water, ETOH, and Glycerin along with Urea in concentrations from 0.1% to 10%, L-Arginine monohydrochlorice salt in concentrations from 0.1% to 20%, and Phosphatidyl Choline in concentrations from 0/1% to 10%. As a non-limiting example, the gel can also have a base of isopropyl myristate. It is understood that other chemicals, compounds, and ingredients can be used is similar combination as described herein above.

Figure 22:
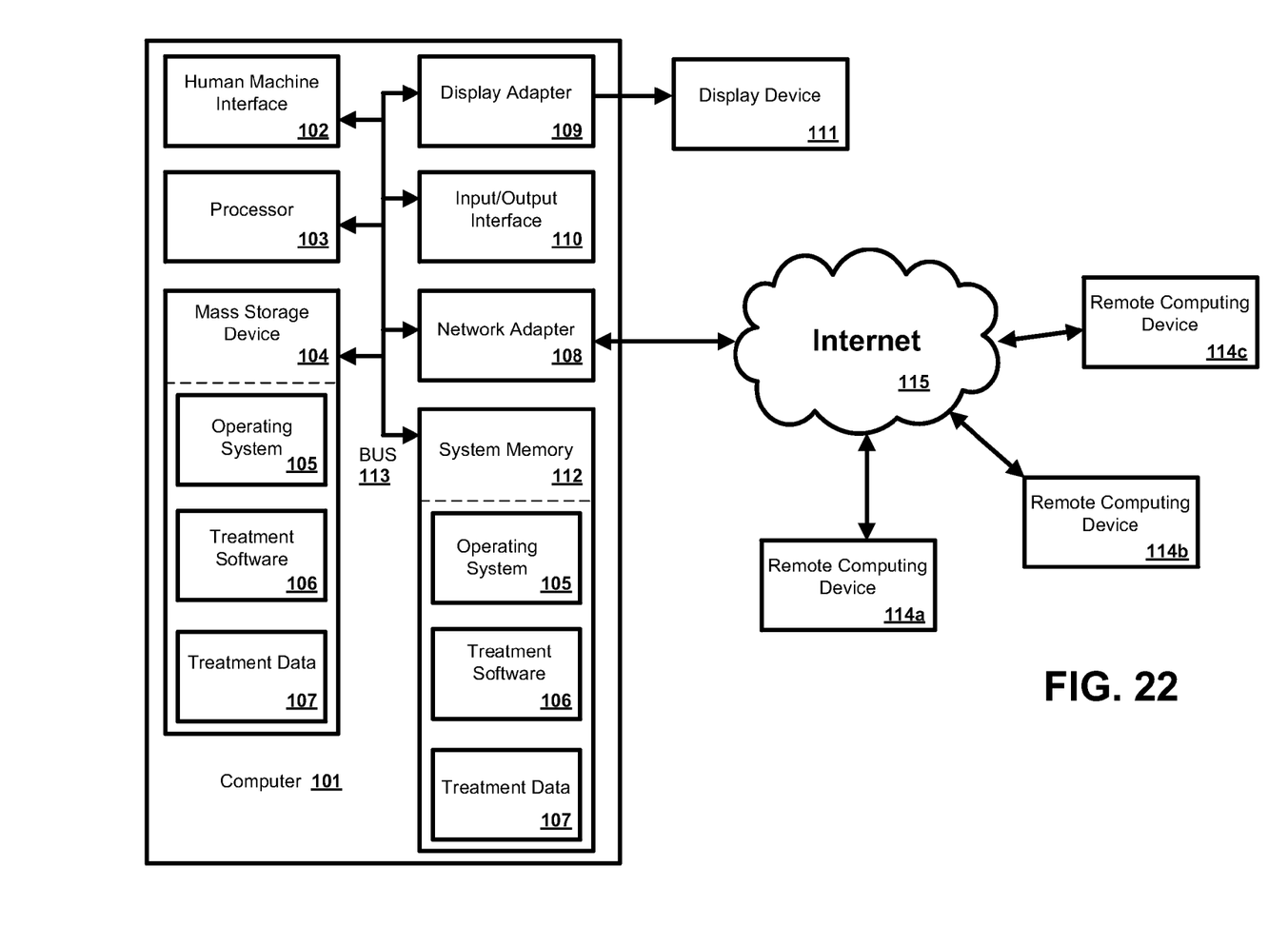
FIG. 22 is a block diagram of an exemplary computing system.

FIG. 22 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a controller or computer 101. As an example, controller 52 can be similar to computer 101. The components of the computer 101 can comprise, but are not limited to, one or more processors or processing units 103, a system memory 112, and a system bus 113 that couples various system components including the processor 103 to the system memory 112. In the case of multiple processing units 103, the system can utilize parallel computing.

The system bus 113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 113, and all buses specified in this description can also be implemented over a wired or wireless network connection and each of the subsystems, including the processor 103, a mass storage device 104, an operating system 105, treatment software 106, treatment data 107, a network adapter 108, system memory 112, an Input/Output Interface 110, a display adapter 109, a display device 111, and a human machine interface 102, can be contained within one or more remote computing devices 114a,b,c at physically separate locations, connected through buses of this form, in effect implementing a fully distributed system.

The computer 101 typically comprises a variety of computer readable media. Exemplary readable media can be any available media that is accessible by the computer 101 and comprises, for example and not meant to be limiting, both volatile and non-volatile media, removable and non-removable media. The system memory 112 comprises computer readable media in the form of volatile memory, such as random access memory (RAM), and/or non-volatile memory, such as read only memory (ROM). The system memory 112 typically contains data such as treatment data 107 and/or program modules such as operating system 105 and treatment software 106 that are immediately accessible to and/or are presently operated on by the processing unit 103.

Figure 1:
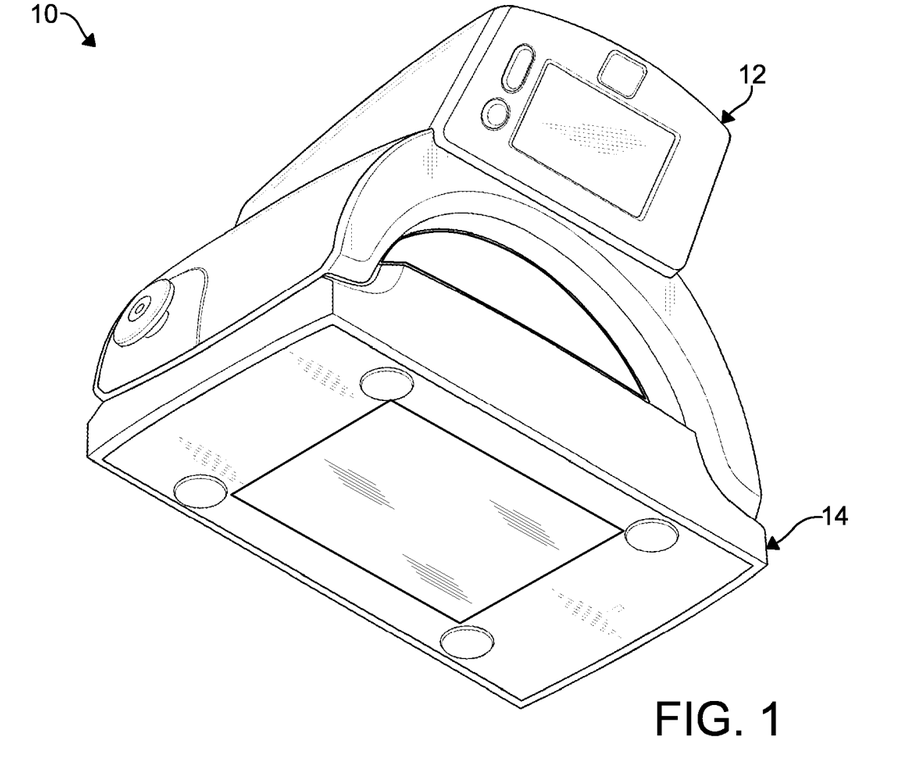
FIG. 1 is a perspective view of a therapy system according to an embodiment of the present invention.
Figure 2:
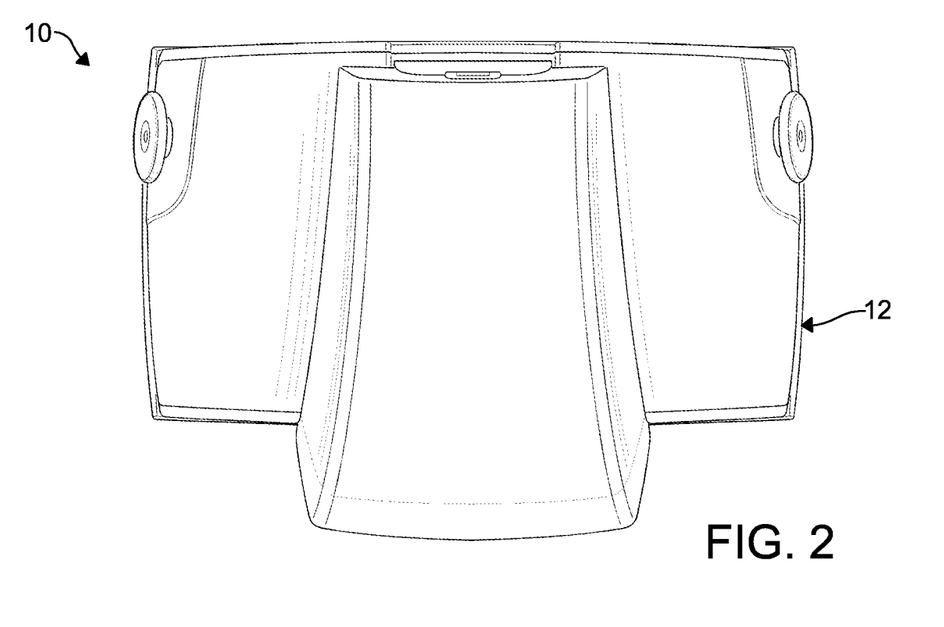
FIG. 2 is a top plan view of the therapy system of FIG. 1.
Figure 3:
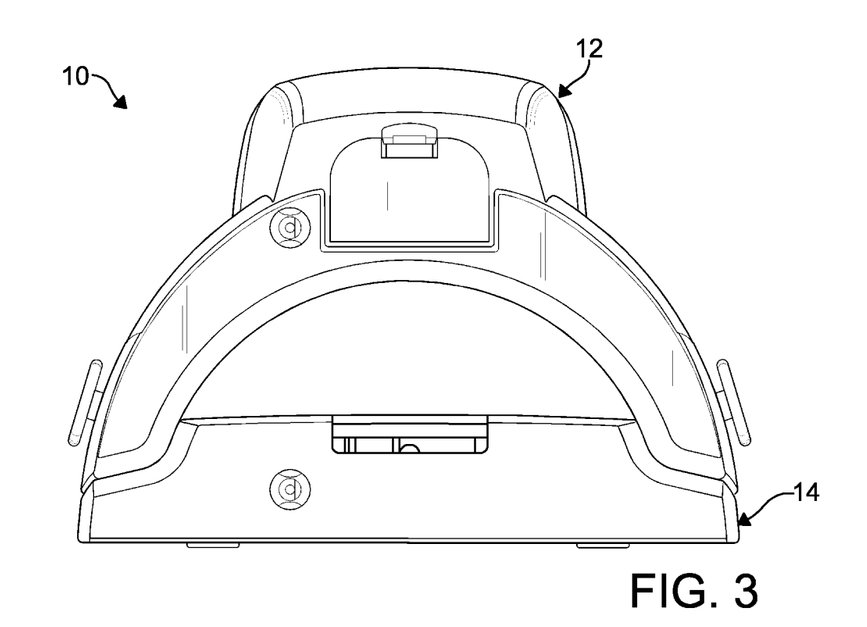
FIG. 3 is a rear elevational view of the therapy system of FIG. 1.
Figure 4:
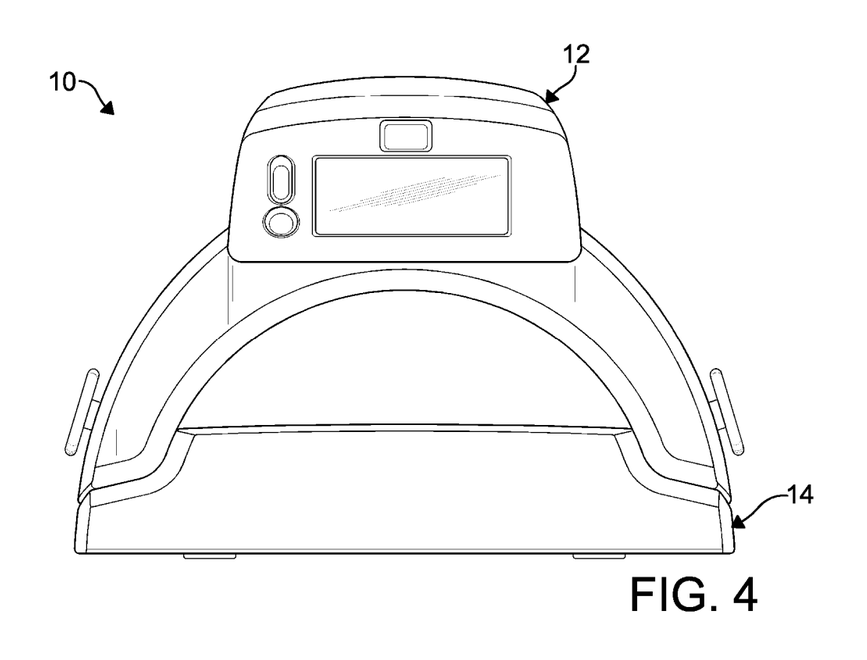
FIG. 4 is a front elevational view of the therapy system of FIG. 1.
Figure 5:
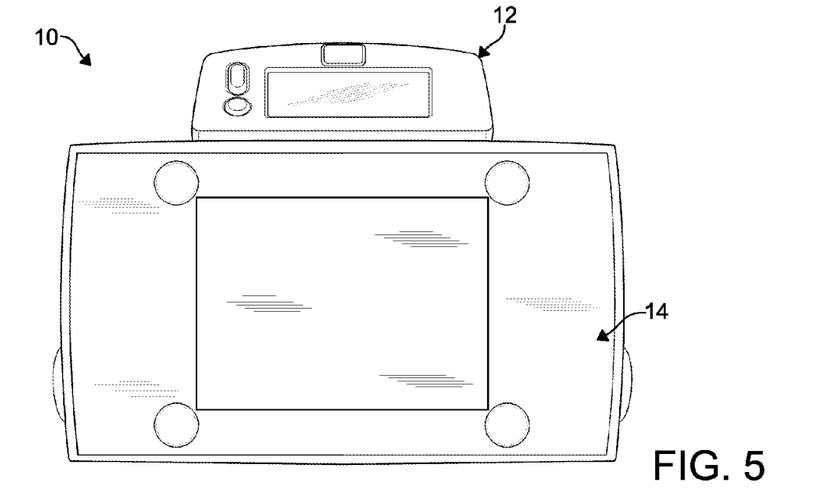
FIG. 5 is a bottom plan view of the therapy system of FIG. 1.
Figures 6, 7:
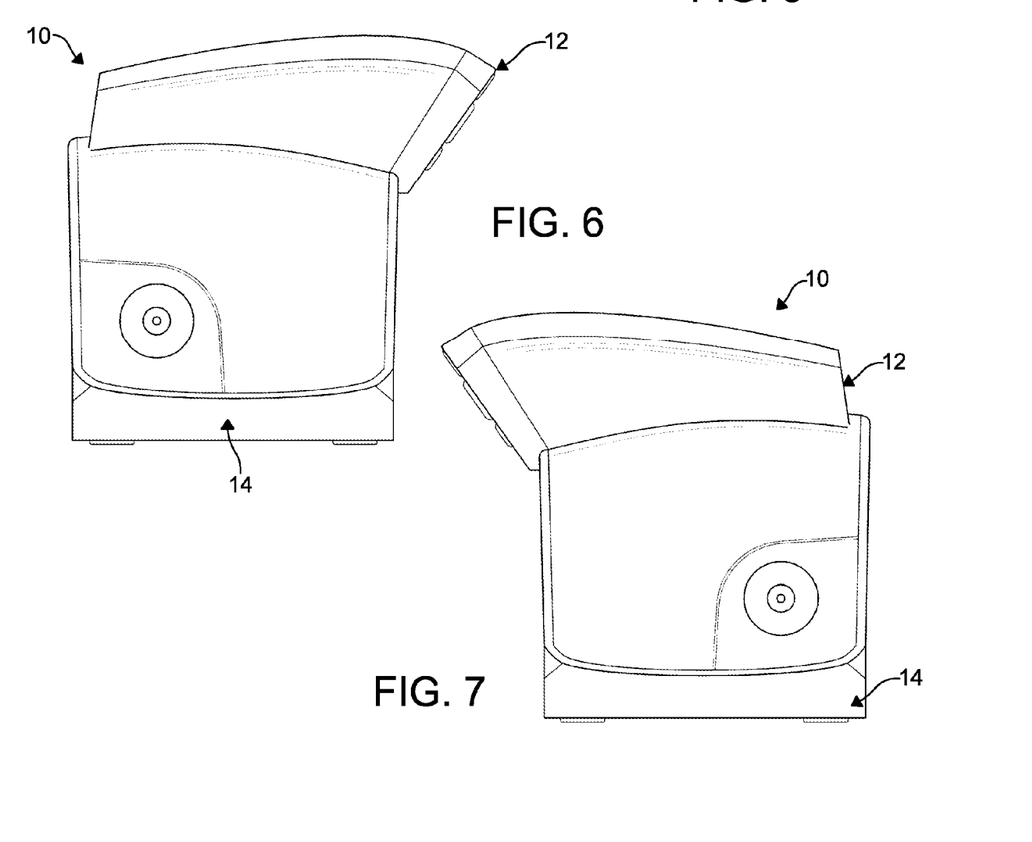
FIG. 6 is a left side elevational view of the therapy system of FIG. 1.
FIG. 7 is a right side elevational view of the therapy system of FIG. 1.
Figure 8:
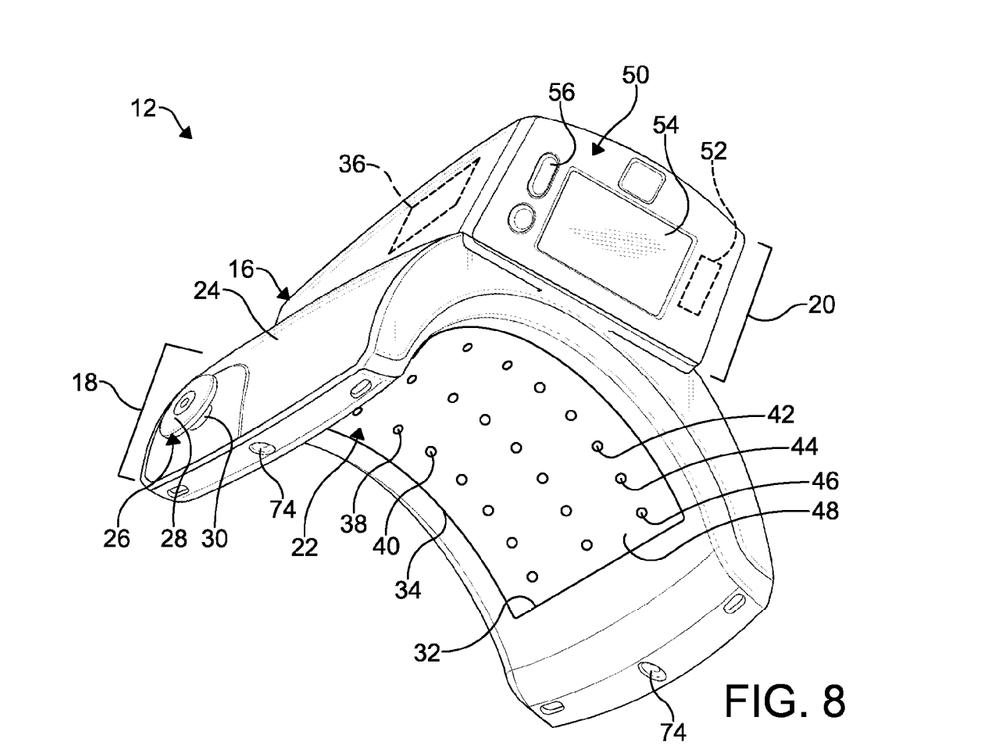
FIG. 8 is a perspective view of a therapy device of the therapy system of FIG. 1.
Figure 9:
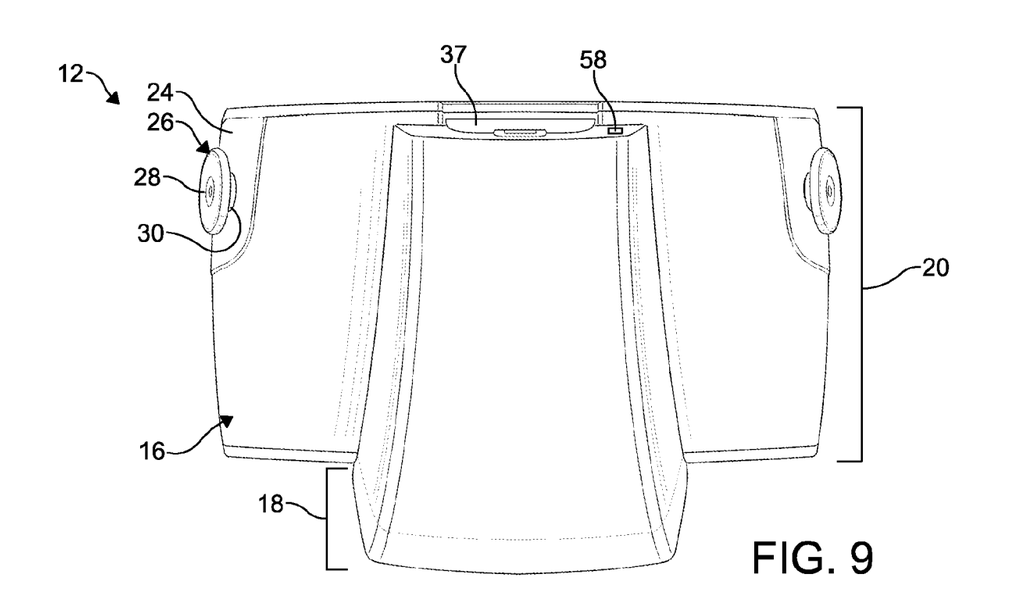
FIG. 9 is a top plan view of the therapy device of FIG. 8.
Figure 10:
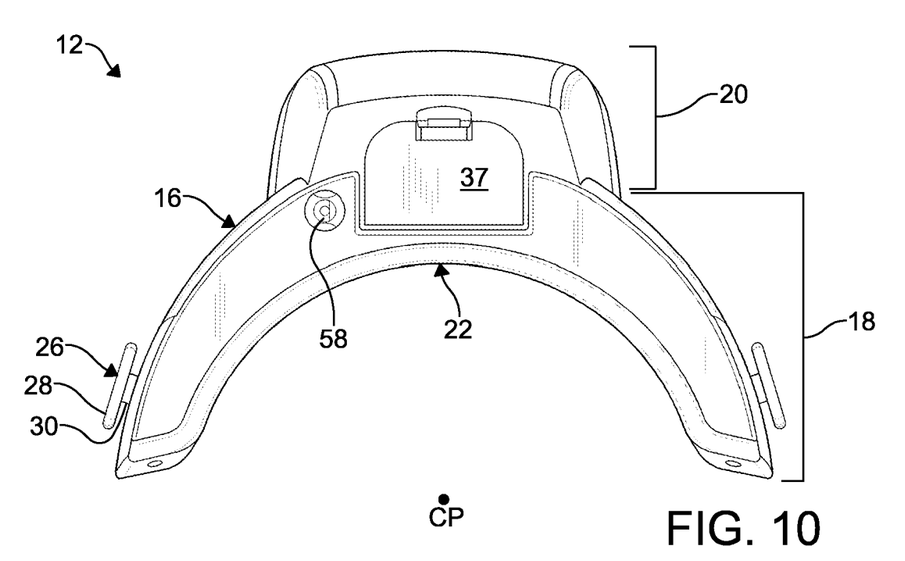
FIG. 10 is a rear elevational view of the therapy device of FIG. 8.
Figure 11:
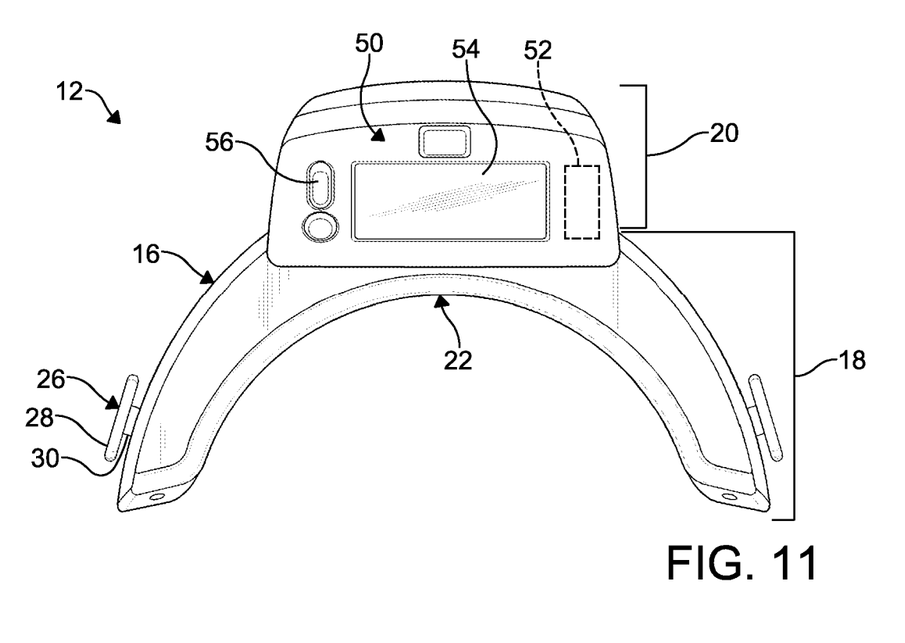
FIG. 11 is a front elevational view of the therapy device of FIG. 8.
Figure 12:
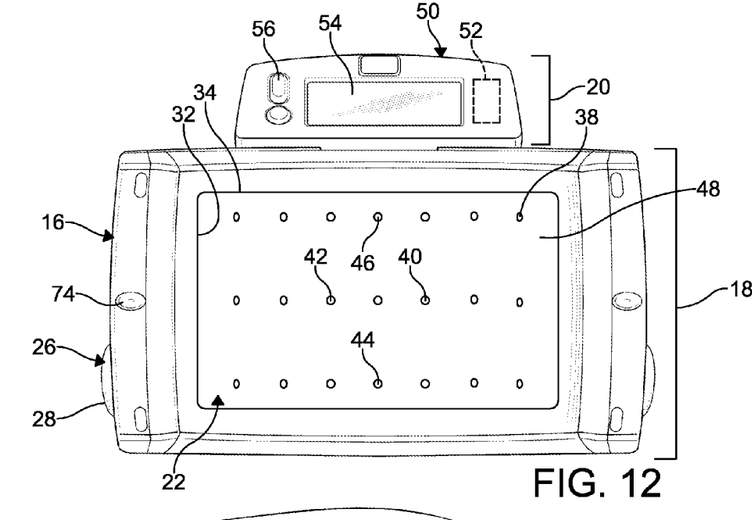
FIG. 12 is a bottom plan view of the therapy device of FIG. 8.
Figures 13, 14:
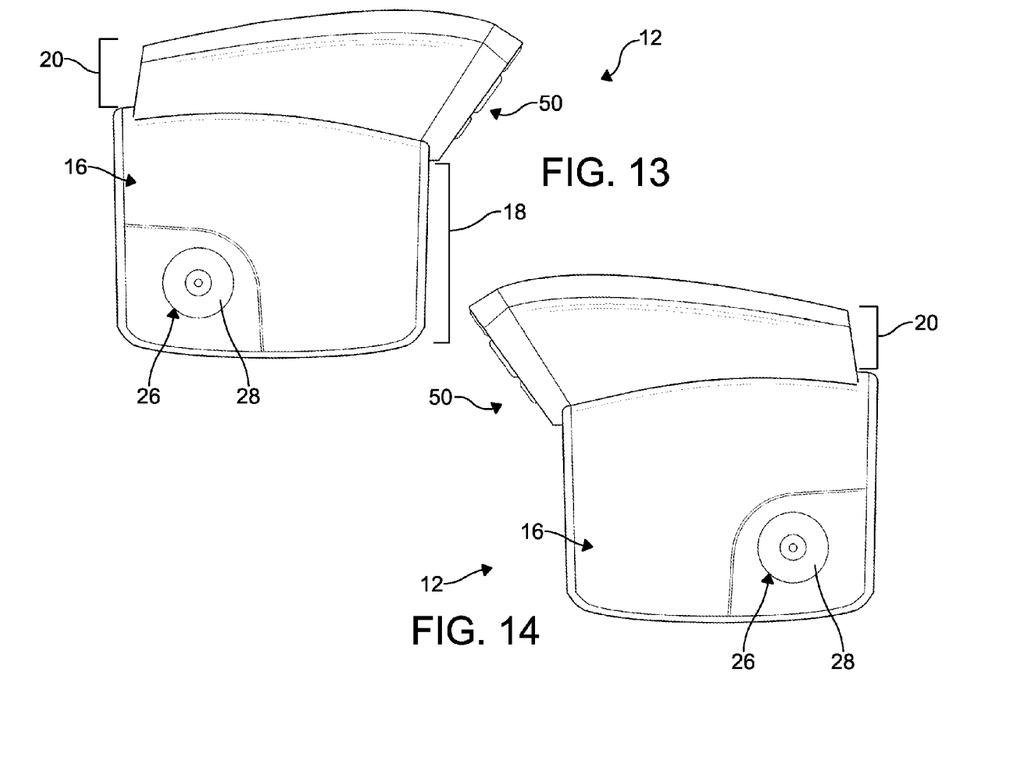
FIG. 13 is a left side elevational view of the therapy device of FIG. 8.
FIG. 14 is a right side elevational view of the therapy device of FIG. 8.
Figure 15:
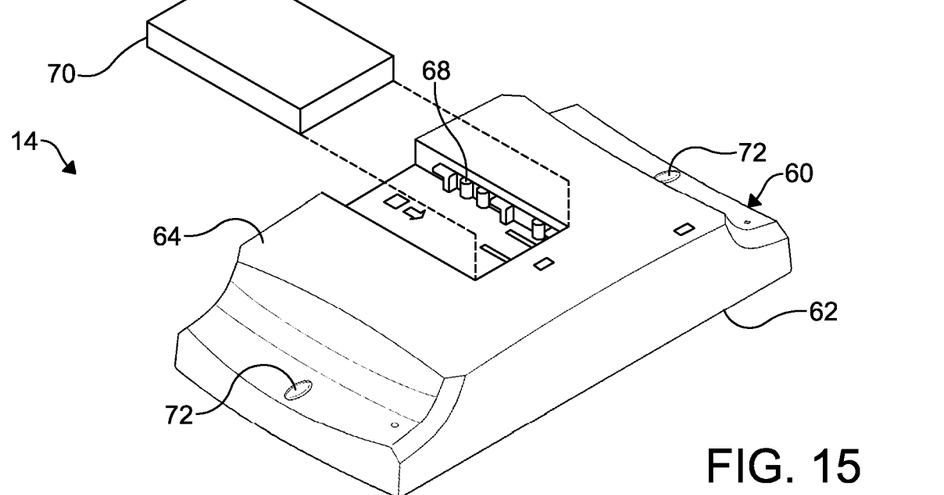
FIG. 15 is a partially exploded perspective view of a base station of the therapy system of FIG. 1.
Figure 16:
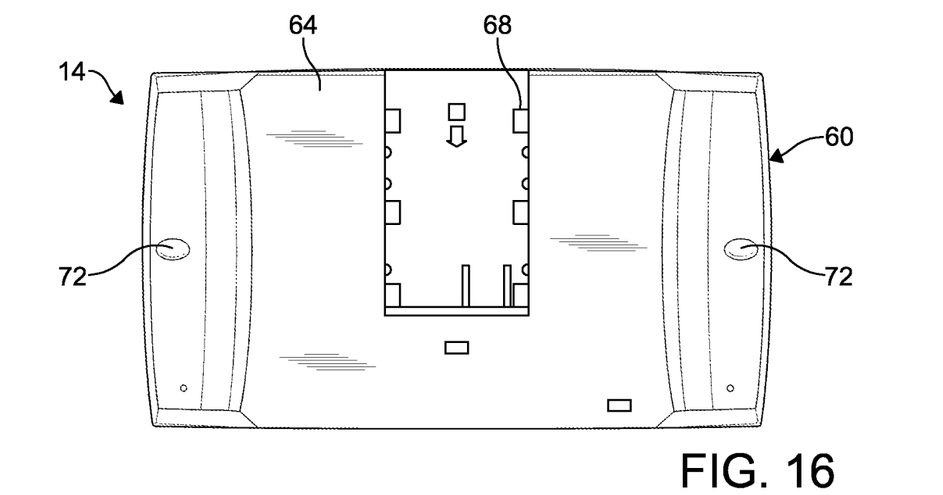
FIG. 16 is a top plan view of the base station of FIG. 15.
Figure 17:
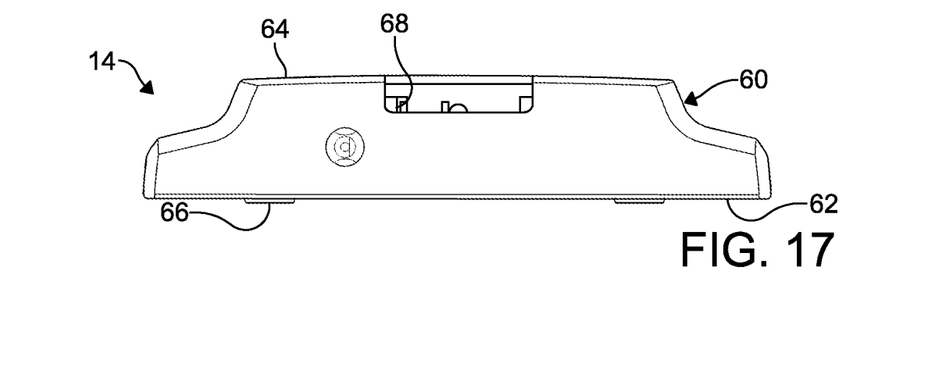
FIG. 17 is a rear elevational view of the base station of FIG. 15.
Figure 18:
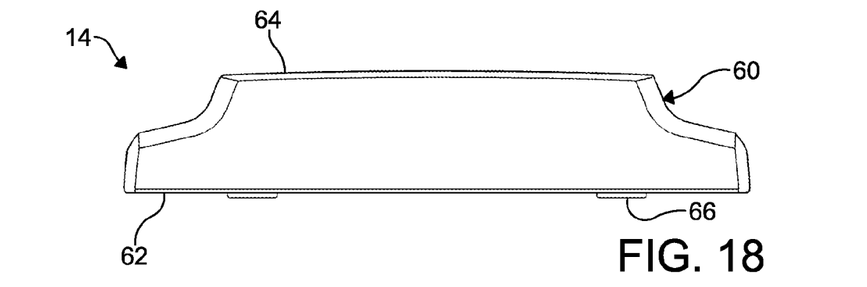
FIG. 18 is a front elevational view of the base station of FIG. 15.
Figure 19:
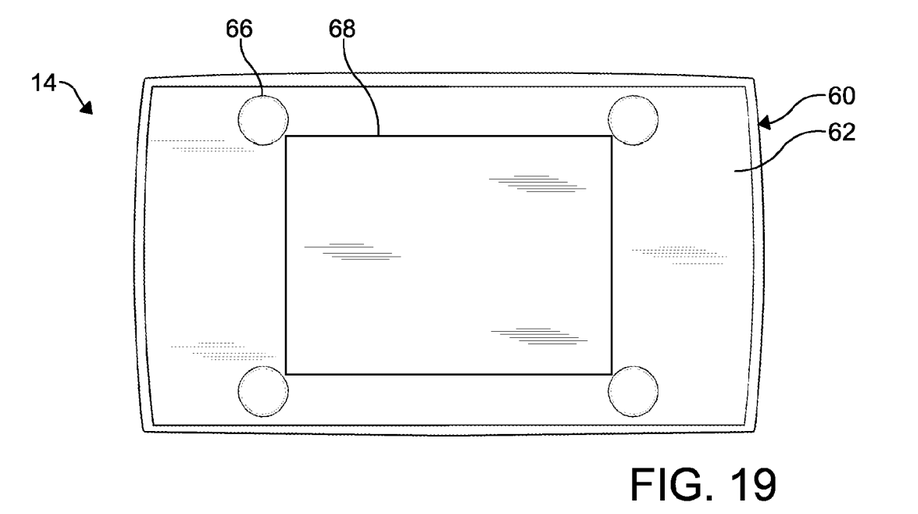
FIG. 19 is a bottom plan view of the base station of FIG. 15.
Figure 20:
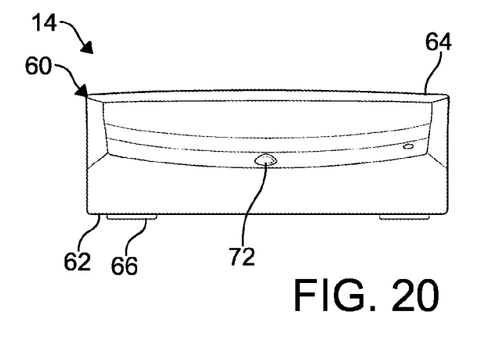
FIG. 20 is a left side elevational view of the base station of FIG. 15.
Figure 21:
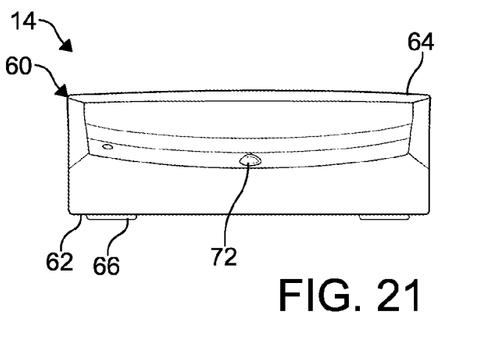
FIG. 21 is a right side elevational view of the base station of FIG. 15.

In another aspect, the computer 101 can also comprise other removable/non-removable, volatile/non-volatile computer storage media. By way of example, FIG. 1 illustrates a mass storage device 104 which can provide non-volatile storage of computer code, computer readable instructions, data structures, program modules, and other data for the computer 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 104, including by way of example, an operating system 105 and treatment software 106. Each of the operating system 105 and treatment software 106 (or some combination thereof) can comprise elements of the programming and the treatment software 106. Treatment data 107 can also be stored on the mass storage device 104. Treatment data 107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 101 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 103 via a human machine interface 102 that is coupled to the system bus 113, but can be connected by other interface and bus structures, such as a parallel port, game port, an IEEE 1394 Port (also known as a Firewire port), a serial port, or a universal serial bus (USB).

In yet another aspect, a display device 111 can also be connected to the system bus 113 via an interface, such as a display adapter 109. It is contemplated that the computer 101 can have more than one display adapter 109 and the computer 101 can have more than one display device 111. For example, a display device can be a monitor, an LCD (Liquid Crystal Display), or a projector. In addition to the display device 111, other output peripheral devices can comprise components such as speakers (not shown) and a printer (not shown) which can be connected to the computer 101 via Input/Output Interface 110. Any step and/or result of the methods can be output in any form to an output device. Such output can be any form of visual representation, including, but not limited to, textual, graphical, animation, audio, tactile, and the like.

The computer 101 can operate in a networked environment using logical connections to one or more remote computing devices 114a,b,c. By way of example, a remote computing device can be a personal computer, portable computer, a server, a router, a network computer, a peer device or other common network node, and so on. Logical connections between the computer 101 and a remote computing device 114a,b,c can be made via a local area network (LAN) and a general wide area network (WAN). Such network connections can be through a network adapter 108. A network adapter 108 can be implemented in both wired and wireless environments. Such networking environments are conventional and commonplace in offices, enterprise-wide computer networks, intranets, and the Internet 115.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of treatment software 106 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The systems and methods of the present disclosure can comprise a treatment platform (e.g., Non-Invasive Neuro-Vascular Stimulation) that can be delivered to painful joints by means of various devices for a variety of applications. In an aspect, the patient/user experience includes pain reduction, accelerated healing, improved mobility, and enhanced performance, and discovery of a variety of cutaneous and intra-articular parameters that are present before, during and after treatment. The treatment platform can incorporate photonic and thermal kinetic energies delivered by a complex mathematical formulas incorporating a plurality (e.g., 14) variable parameters among which include: i) Photonic Energy comprised of multiple wave lengths, sequencing, patterns, refresh rates, energies, and duty cycles, ii) Thermal Kinetic Energy, dynamically changing thermal delivery properties, and iii) Subliminal Sonic Message (SSM). Each user can receive a personalized Veriscription or "electronic-prescription" that is formulated specifically to a body area and condition. Moreover, the system can also collect an assortment of data from the treatment surface of the user and insert treatment variables in a treatment algorithm for delivery to the body.

A delivery implement can comprise computer chips and/or microprocessors which are programmed with multiple parameters and functions that activate and sequence specialized LEDs (light emitting diodes) and other electronic components on the treatment surface.

The treatment surface, located on the treatment module portion of the delivery implement can be equipped with specialized technology that integrates looped biofeedback information. The implement/device can assimilate multiple afferent and efferent parameters that subsequently direct and effect the afore mentioned complex treatment administered to the surface of the body.

In an aspect, mode selection enables the user to select the treatment that relates to the nature and location of their condition. For example, an injury or condition of a specific body area (i.e. the knee joint) of less than 30 hours duration requires a unique energy and sequencing pattern that integrates a specific heat range.

When the treatment surface is applied directly to the skin the energies used in the systems and methods promotes various chemical and philological reactions which can also be utilized to help quantify the level of benefit the treatment is providing. For example, it is envisioned that software in the operating system could be enhanced to include base line sensory and performance metrics measured and recorded before and after treatment. This information would demonstrate the benefit the user had received from the treatment therapy session, and can then be utilized to formulate and customize subsequent therapies.

The unique clinical advantages of the present systems and methods comprise: i) safe treatment of pain and limited performance, ii) highly effective (>85%) pain relief and improved mobility iii) no adverse side-effects, iv) prevention of tachyphylaxis (adaptation by the body), and v) accelerated healing and rehabilitation.

Current methodologies for data collection of pain and joint discomfort are inadequate. Ongoing research may provide data on chemical, structural and physiological events when healing or an improvement in joint mobility takes place. For example, heat generated by an affected joint may dissipate move or change character over the course of the treatment session. Other events may include changes in chemical parameters such as pH, nitric oxide, lactic acid, fluid volume, fluid density, and etc. Furthermore, the delivery technology of the disclosed systems and methods can be enhanced to offer a "heat mapping" technology design to detect and collect certain changes in the treatment site.

This can include muscle tension or fibrillation detection or the emission of chemicals from the skin surface. This can contribute to the detoxification of the joint and cessation of the sensation of pain during and after the treatment session. These improvements can provide more customized and personalized treatment to improve the condition of the user, collect data useful to medical research, and aid in therapeutic and diagnostic arenas.

It is intended that any enhancements as discussed herein would be simple to use with an intuitive interface that would require few instructions. Furthermore, a hand-held unit could be delivered to the user without the software installed. Then, at the time of purchase, the user could follow simple instructions provided to download activation software that could be customized for their use by means of selection of various parameters. The user could also select an automatic function to upload their treatment data to a database for additional review by their physician or for their personal review.

Periodically, the user can also confirm that their instrument is operating at peak level so they could elect to schedule a period diagnostic "tune up" or test where in the unit is connected to an online interface to conduct a testing routine. The user could also elect to install the latest version of their software. They may be offered as an enhanced feature for a monthly subscription etc.

It is realized that multiple areas of the human body have different and often unique anatomical composition, physiology, and form. Applications employing the disclosed technology will vary between other anatomical areas of the body and between species. This technology is envisioned and claimed to be unique for different species such as canine, equine, avian, reptilian, and etc. Therefore, it should be understood that treatment energy ingredients, treatment parameters, composition, and delivery algorithms can be unique and proprietary to species, area, and condition.

In an aspect, a handheld treatment device can be in communication with a base station for charging, data transfer, and/or storage. As an example, the base station or docking station can provide processors, memory, storage, network connectivity, and/or automated detections of user port and sign in with bi-directional information exchange and period update of software or repair and user diagnostics.

In an aspect, the concept of "wisdom of crowds" suggests that decisions resulting in data from a large population are often better than that of a single member. In addition, cloud technology enables information to be collected in one access point for multiple users across various platforms.

In an aspect, the system and method of the present disclosure can be used to create a pain search engine based on the wisdom of crowds in a depository where it can be evaluated, articulated, and delivered to other members in an online technotherapy setting.

As an example, a technotherapy device (e.g., therapy device 12) can be distributed without any operating instructions installed at the time of purchase. The device could be delivered to users at a lower cost and when the user wished to use the device, the use would be required to apply for registration, at which time certain software would be installed in the device by means of a Wi-Fi or other communication connection. Information can be transmitted to the cloud depository where the software and user records were stored. Such software would have varying technological and therapeutic capabilities. For example, a user may wish to op for therapy for a certain problem like arthritis of the knee. This software may be available at a certain cost per month or cost per therapy session. And the pricing could be adjusted based on the services provided; from therapy only to therapy with data capture and diagnostic review. In essence, the user could select from a menu of technotheraputic services.

In an aspect, the present system can provide the basis of uniform data collection resulting in greater compliance by the patient population resulting in more desirable patient outcomes. As an example, the following process can summarizes an exemplary treatment procedure:

1. therapy device is connected to a network;
2. a self-diagnosis patient profile or patient profile is generated;
3. patient record is populated with user information;
4. a selection of therapeutic services (e.g., by subscription) is received;
5. initial user interface is downloaded to the device;
6. device can be calibrate for a particular user, wherein the device collects various information from the skin surface which is uploaded to the host application;
7. data is presented to the host application which conducts various evaluation analysis and presents the data to the "pain search engine" comparing the users data with that of other users in the "pain cloud;"
8. generating a search from the "pain universe" and creating a customized treatment for the user for the initial treatment session;
9. data is collected from the skin surface or other data collection parameters that may be available with the user's level of service and scored and compared with the data from the pain cloud Veriscription population; and
10. user's record is updated producing reports for diagnostic, reporting, and evaluation purpose.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

From the foregoing description, one ordinarily skilled in the art can easily ascertain the essential characteristics of this invention and, without departing from the spirit and scope thereof, make various changes and modifications to the invention to adapt it to various usages and conditions. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A digital anti-inflammatory apparatus comprising:
a rigid housing with a lower portion and an upper portion, the lower portion of the housing having a curvilinear shape;
a flexible circuit board disposed in a cavity formed in the lower portion of the housing;
a light source configured to emit dynamic photonic energy;
a thermal element configured to emit dynamic thermal kinetic energy;
a sonic element configured to emit dynamic subliminal ultrasonic energy;
a controller disposed in the housing, the controller in communication electrically coupled with the light source, the thermal element, and the sonic element to vary one or more parameters of the light source, the thermal element, and the sonic element, wherein the controller is configured to control the characteristics of one or more of the dynamic photonic energy, the dynamic thermal kinetic energy, and the dynamic subliminal ultrasonic energy emitted respectively thereby; and
a multisensory system comprising a first sensor, a second sensor, and a third sensor in electrical communication with the circuit board and the controller to form a feedback loop, wherein the first sensor is configured to measure one or more chemical elements, wherein the second sensor is configured to measure one or more physical elements, wherein the one or more measured physical elements comprises one or more of fluid volume and fluid density, wherein the third sensor is configured to measure one or more physiological elements, wherein the controller learns characteristics of a user based on the measurements from the first sensor, the second sensor, and the third sensor and calculates an electronic prescription of treatment, and wherein the controller provides electrical energy to one or more of the light source, the heating element, and the sonic element in response to the prescription to customize treatment for the user.

2. The apparatus of claim 1, further comprising a mechanism configured for securing the therapy device to a user during use.

3. The apparatus of claim 2, wherein the securing mechanism includes a pair of generally circular discs.

4. The apparatus of claim 1, further comprising a user interface in electrical communication with the controller.

5. The apparatus of claim 1, wherein the controller is configured to control a pattern and a rate at which one or more of the light source, the thermal element, and the sonic element are energized.

6. The apparatus of claim 1, wherein the controller is configured to selectively and independently provide electrical energy for energizing one or more of the light source, the thermal element, and the sonic element based upon a predefined treatment for a predetermined area of a body of a user.

7. The apparatus of claim 1, wherein the one or more measured chemical elements comprises one or more of pH, nitric oxide, and lactic acid.

8. The apparatus of claim 1, wherein the one or more measured physiological elements are measured using electromyography.

9. A digital anti-inflammatory apparatus comprising:
a rigid housing with a lower portion and an upper portion, the lower portion of the housing having a curvilinear shape;
a flexible circuit board disposed in a cavity formed in the lower portion of the housing;
a light source configured to emit dynamic photonic energy;
a thermal element configured to emit dynamic thermal kinetic energy;
a sonic element configured to emit dynamic subliminal ultrasonic energy;
a controller disposed in the housing, the controller in communication electrically coupled with the light source, the thermal element, and the sonic element to vary one or more parameters of the light source, the thermal element, and the sonic element, wherein the controller is configured to control the characteristics of one or more of the dynamic photonic energy, the dynamic thermal kinetic energy, and the dynamic subliminal ultrasonic energy emitted respectively thereby;
a multisensory system comprising a first sensor, a second sensor, and a third sensor in electrical communication with the circuit board and the controller to form a feedback loop, wherein the first sensor is configured to measure one or more chemical elements, wherein the second sensor is configured to measure one or more physical elements, wherein the one or more measured physical elements comprises one or more of fluid volume and fluid density, wherein the third sensor is configured to measure one or more physiological elements, wherein the controller learns characteristics of a user based on the measurements from the first sensor, the second sensor, and the third sensor and calculates an electronic prescription of treatment, and wherein the controller provides electrical energy to one or more of the light source, the heating element, and the sonic element in response to the prescription to customize treatment for the user; and
a network component to facilitate communication via a network.

10. The apparatus of claim 9, wherein the one or more measured chemical elements comprises one or more of pH, nitric oxide, and lactic acid.

11. The apparatus of claim 9, wherein the one or more measured physiological elements are measured using electromyography.

12. The apparatus of claim 9, wherein the network comprises a local area network.

13. The apparatus of claim 9, wherein the network comprises the Internet.

* * * * *